US00PP37705P2

(12) United States Plant Patent
Heuger

(10) Patent No.: US PP37,705 P2
(45) Date of Patent: Sep. 22, 2026

(54) ***HELLEBORUS* PLANT NAMED 'HF 1120'**

(50) Latin Name: ***HHelleborus* x *nigercors* x *Helleborus* x *hybridus***
Varietal Denomination: Hf 1120

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 19/397,949

(22) Filed: Nov. 23, 2025

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./263.1, 439
See application file for complete search history.

(56) References Cited

U.S. PATENT DOCUMENTS

PP22,018 P2 * 7/2011 Heuger ..... A01H 6/72
Plt./439

* cited by examiner

*Primary Examiner* — Karen M Redden
(74) *Attorney, Agent, or Firm* — C. Anne Whealy

(57) ABSTRACT

A new and distinct cultivar of *Helleborus* plant named 'HF 1120', characterized by its upright to outwardly spreading and mounded plant habit; moderately vigorous to vigorous growth habit; dark green-colored leaflets; freely flowering habit; flowers with white and purplish red bi-colored sepals; and good garden performance.

2 Drawing Sheets

Figure 1:
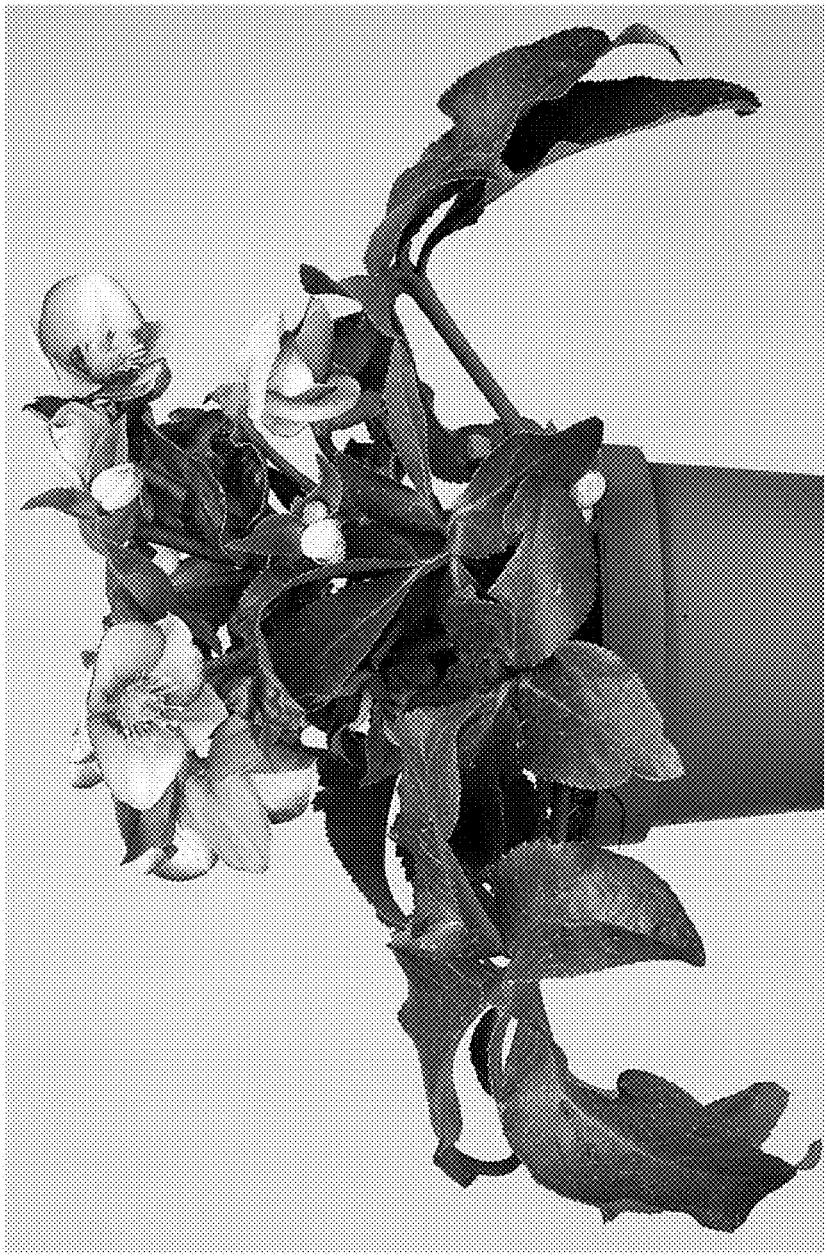

Botanical designation: *Helleborus* x *nigercors* X *Helleborus* x *hybridus*.
Cultivar denomination: 'HF 1120'.

CROSS-REFERENCED TO CLOSELY-RELATED APPLICATIONS

A European Community Plant Breeder's Rights application for the instant plant was filed by the Inventor/Applicant, Mr. Josef Heuger of Glandorf, Germany, on Nov. 30, 2024, application number 2024/2899. Foreign priority is not claimed to this application.

A United Kingdom Plant Breeder's Rights application for the instant plant was filed by the Inventor/Applicant, Mr. Josef Heuger of Glandorf, Germany, on Aug. 29, 2025, application number 30/984. Foreign priority is not claimed to this application.

BACKGROUND OF THE INVENTION

The present invention relates to a new and distinct cultivar of *Helleborus* plant, botanically known as *Helleborus* x *nigercors* X *Helleborus* x *hybridus* and hereinafter referred to by the name 'HF 1120'.

The new *Helleborus* plant is a product of a planned breeding program conducted by the Inventor in Glandorf, Germany. The objective of the breeding program was to create new uniform *Helleborus* plants with unique leaf and flower coloration and tolerance to biotic and abiotic stresses.

The new *Helleborus* plant originated from a cross-pollination conducted by the Inventor in Glandorf, Germany in December, 2016 of a proprietary selection of *Helleborus* x *nigercors* identified as code number 065, not patented, as the female, or seed, parent and a proprietary selection of *Helleborus* x *hybridus* identified as code number 16-32, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December, 2018.

Asexual reproduction of the new *Helleborus* plant by in vitro axillary meristem culture in a controlled environment in Glandorf, Germany since September, 2019 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HF 1120'. These characteristics in combination distinguish 'HF 1120' as a new and distinct *Helleborus* plant:

1. Upright to outwardly spreading and mounded plant habit.
2. Moderately vigorous to vigorous growth habit.
3. Dark green-colored leaflets.
4. Freely flowering habit.
5. Flowers with white and purplish red bi-colored sepals.
6. Good garden performance.

Plants of the new *Helleborus* differ from plants of the female parent selection in the following characteristics:

1. Leaflets of plants of the new *Helleborus* are lighter green in color than leaflets of plants of the female parent selection.

2. Flower sepals of plants of the new *Helleborus* are white and purplish red bi-colored whereas flower sepals of plants of the female parent selection are creamy white in color.

Plants of the new *Helleborus* differ from plants of the male parent selection in the following characteristics:

1. Leaflets of plants of the new *Helleborus* are lighter green in color than leaflets of plants of the male parent selection.
2. Flower sepals of plants of the new *Helleborus* are white and purplish red bi-colored whereas flower sepals of plants of the male parent selection are pink in color.

Plants of the new *Helleborus* can also be compared to plants of *Helleborus* x *nigercors* 'COSEH 750', disclosed in U.S. Plant Pat. No. 22,018. In side-by-side comparisons, plants of the new *Helleborus* differ primarily from plants of 'COSEH 750' in the following characteristics:

1. Leaflets of plants of the new *Helleborus* are lighter green in color than leaflets of plants of 'COSEH 750'.
2. Flower sepals of plants of the new *Helleborus* are white and purplish red bi-colored whereas flower sepals of plants of 'COSEH 750' are light green to white in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HF 1120' grown in a container.

Figure 2:
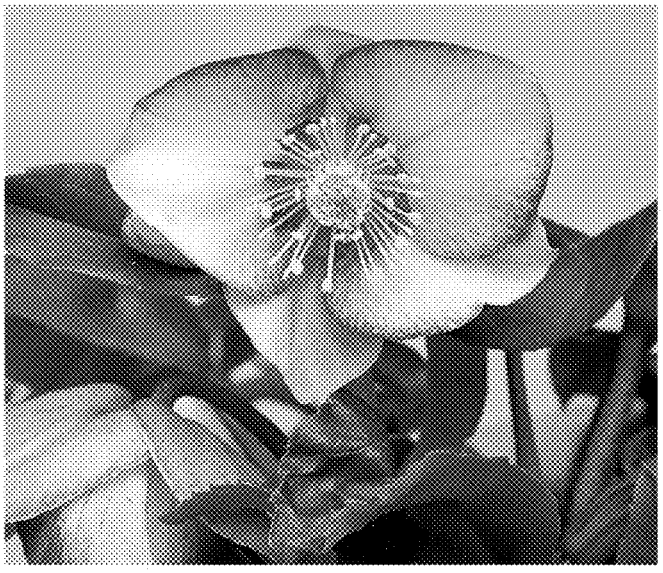

The photograph at the top of the second sheet (FIG. 2) is a close-up view of a typical flower of 'HF 1120'.

Figure 3:
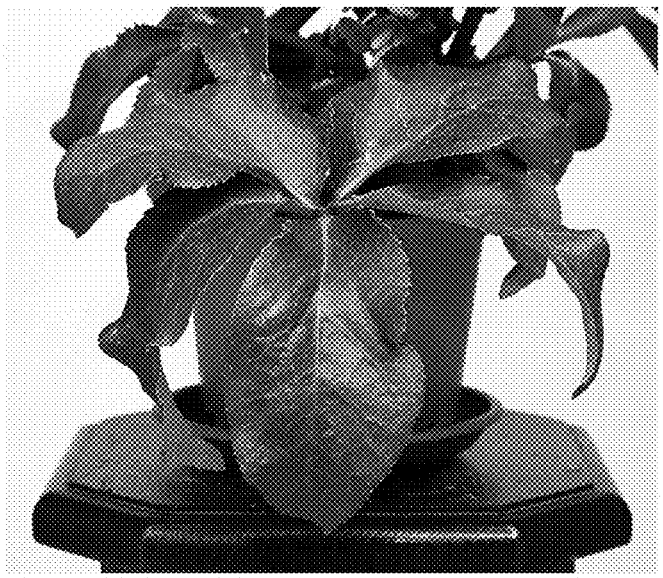

The photograph at the bottom of the second sheet (FIG. 3) is a close-up view of typical leaflets of 'HF 1120'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 32° C. and night temperatures ranged from 5° C. to 12° C. Plants were 48 weeks old when the photographs were taken and 14 months old when the detailed description was taken. In the following description, color references are made to The Royal Horticultural Society Colour Chart, Sixth Edition (2019 reprint), except where general terms of ordinary dictionary significance are used.

Botanical classification: *Helleborus* x *nigercors* X *Helleborus* x *hybridus* 'HF 1120'.

Parentage:

*Female, or seed, parent*.—Proprietary selection of *Helleborus* x *nigercors* identified as code number 065, not patented.

*Male, or pollen, parent*.—Proprietary selection of *Helleborus* x *hybridus* identified as code number 16-32, not patented.

Propagation:

*Type*.—In vitro axillary meristem culture.

*Time to initiate roots, winter*.—About 55 days at temperatures about 12° C.

*Time to produce a rooted young plant, winter*.—About 170 days at temperatures ranging from about 4° C. to 15° C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to outwardly spreading and mounding plant habit with flowers held above the foliar plane; plant shape, roughly flattened globular to globular; moderately vigorous to vigorous growth habit and moderate growth rate.

*Plant height, soil level to top of foliar plane*.—About 16 cm.

*Plant height, soil level to top of flowers*.—About 25 cm.

*Plant diameter* (*area of spread*).—About 41 cm.

Leaf description:

*Arrangement*.—Leaves arranged in a basal rosette; leaves palmately compound with typically five leaflets per leaf.

*Leaf length*.—About 19.5 cm.

*Leaf width*.—About 21.8 cm.

*Leaflet length*.—About 14 cm.

*Leaflet width*.—About 7.1 cm.

*Leaf shape*.—Palmate; roughly reniform in outline.

*Leaflet shape*.—Ovate to elliptic; lowest leaflets occasionally cleft.

*Leaflet apex*.—Acute.

*Leaflet base*.—Attenuate.

*Leaflet margin*.—Serrate; slightly coarsely undulate.

*Leaflet texture and luster, upper and lower surfaces*.—Smooth, glabrous; coriaceous and tough; slightly glossy.

*Leaflet venation pattern*.—Pinnate and reticulate.

*Leaflet color*.—Developing leaflets, upper surface: Close to 137D; at the base, close to 183A and 183B. Developing leaflets, lower surface: Close to a blend of 143C and 144A; midvein, close to 165A. Fully developed leaflets, upper surface: Close to a blend of 147A and N189A; at the base, tinged with close to 200B and 200C; venation, close to 144A. Fully developed leaflets, lower surface: Close to 147B; venation, close to 146C.

*Petioles*.—Length: About 14.2 cm. Diameter: About 6 mm. Strength: Strong. Texture and luster, upper and lower surfaces: Smooth, glabrous; moderately glossy. Color, upper surface: Close to 138A with dots, close to N186C. Color, lower surface: Close to 143B with dots, close to N186C and 176A to 176C.

Flower description:

*Flower shape and habit*.—Single rotate bowl-shaped flowers arranged in panicles; freely flowering habit with about eleven flowers per inflorescence and about 90 flowers and flower buds per plant; flowers face outwardly to slightly nodding.

*Fragrance*.—None detected.

*Natural flowering season*.—Plants begin flowering about ten months after planting; plants flower naturally from early winter into the late winter in Germany.

*Flower longevity on the plant*.—About ten days; sepals persistent, other flower parts are not persistent.

*Flower buds*.—Length: About 2.1 cm. Diameter: About 1.5 cm. Shape: Broadly ovate. Texture and luster: Smooth, glabrous; matte. Color: Close to 145B and 145C; at the margins, close to 187D.

*Inflorescence height* (*including peduncle*).—About 23.8 cm.

*Inflorescence diameter*.—About 17.3 cm.

*Flower diameter*.—About 7.6 cm.

*Flower depth*.—About 2.6 cm.

*Petals*.—All petals are transformed into nectaries.

*Sepals*.—Quantity and arrangement: About five, arranged in a single whorl. Length: About 5.4 cm. Width: About 4.1 cm. Shape: Broadly ovate to close to reniform; slightly concave. Apex: Obtuse. Base: Cuneate. Margin: Entire. Texture and luster, upper surface: Smooth, glabrous; matte. Texture and luster, lower surface: Smooth, glabrous; slightly glossy. Color, upper sepals: When opening, upper surface: Close to 157A and 157B; towards the apex and margins, close to 61A; at the base, close to 150C. When opening, lower surface: Close to 155C; towards the apex and margins, close to 59B; at the base, close to 150C; venation, close to 61A. Fully opened, upper surface: Close to 155A; towards the apex and margins, close to 71A and 71B; distal blotch, close to 150D; at the base, close to 150C to 150D. Fully opened, lower surface: Close to 155A; towards the apex and margins, close to 61A; at the base, close to 145B; venation, close to 61B. Color, lower sepals: When opening, upper surface: Close to 145B to 145D; towards the apex and margins, close to 71C and 71D. When opening, lower surface: Close to 145B to 145D; towards the apex and margins, close to 71C and 71D. Fully opened, upper surface: Close to 145A to 145C; towards the apex and margins, close to 71A and 71B. Fully opened, lower surface: Close to 145A to 145B; towards the apex and margins, close to 61A.

*Flower bracts*.—Quantity per flower: Typically one or two. Length: About 7.7 cm. Width: About 4.3 cm. Shape: Broadly ovate. Apex: Acute. Base: Truncate to cuneate. Margin: Serrate; moderately to strongly coarsely undulate. Color, upper surface: Close to NN137A. Color, lower surface: Close to 147B.

*Peduncles*.—Length: About 16.1 cm. Diameter: About 8 mm to 12.5 mm. Aspect: About 25° from vertical. Strength: Strong. Texture and luster: Smooth, glabrous; slightly glossy. Color: Close to 144A; moderately to heavily covered with fine dots, close to 187B.

*Pedicels*.—Length: About 3.3 cm. Diameter: About 3 mm. Aspect: About 20° from peduncle axis. Strength: Moderately strong. Texture and luster: Smooth, glabrous; slightly to moderately glossy. Color: Close to 150D; moderately marbled with close to 181D.

*Reproductive organs*.—Stamens: Quantity per flower: About 100. Filament length: About 1.7 cm. Filament color: Close to 155A. Anther shape: Double and broadly reniform; basifixed. Anther size: About 1.75 mm by 2.5 mm. Anther color: Close to 154C. Pollen amount: Sparse. Pollen color: Close to 4D. Pistils: Quantity per flower: About three to six. Pistil length: About 1.2 cm. Stigma diameter: About 0.3 mm. Stigma shape: Club-shaped. Stigma color: Close to 150D. Style length: About 1.15 cm. Style color: Close to a blend of 63B and 186B. Ovary color: Close to 145A; axial rib, close to 157C. Nectaries (transformed petals): Quantity per flower: About 13 to 16. Length: About 1 cm. Diameter: About 4 mm. Shape: Tubular, flattened; apices, obtuse. Texture and luster, inner and outer surfaces: Smooth, glabrous; slightly glossy. Color, immature, inner and outer surfaces: Close to N144C; towards the apex, tinged with close to 180A. Color, mature, inner and outer surfaces: Close to N144A; distally, close to 153D and towards the apex, close to 180B; with subsequent development, distally, color becoming closer to 153C. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35° C. and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HF 1120' as herein illustrated and described.

* * * * *